United States Patent
Yu et al.

(10) Patent No.: US 9,416,410 B2
(45) Date of Patent: Aug. 16, 2016

(54) CUTOFF POINT DELTA CT. METHOD FOR HER2 PCR TESTING IN BREAST CANCER

(71) Applicant: Genetics Development Corporation, Lake Bluff, IL (US)

(72) Inventors: Rong Yu, Pearland, TX (US);
Kung-ying Chiu, Chicago, IL (US);
Shau-zou Lu, Lake Bluff, IL (US)

(73) Assignee: Genetics Development Corporation, Lake Bluff, IL (US)

( * ) Notice: Subject to any disclaimer, the term of this patent is extended or adjusted under 35 U.S.C. 154(b) by 0 days.

(21) Appl. No.: 13/765,701

(22) Filed: Feb. 13, 2013

(65) Prior Publication Data

US 2014/0335525 A1 Nov. 13, 2014

Related U.S. Application Data

(60) Provisional application No. 61/598,416, filed on Feb. 14, 2012.

(51) Int. Cl.
| | | |
|---|---|---|
| *C12Q 1/68* | (2006.01) | |
| *A61F 2/24* | (2006.01) | |
| *A61L 27/36* | (2006.01) | |
| *G06F 19/18* | (2011.01) | |

(52) U.S. Cl.
CPC .............. *C12Q 1/686* (2013.01); *A61F 2/2412* (2013.01); *A61L 27/3604* (2013.01); *A61L 2430/20* (2013.01); *G06F 19/18* (2013.01)

(58) Field of Classification Search
None
See application file for complete search history.

(56) References Cited

U.S. PATENT DOCUMENTS

2011/0306055 A1* 12/2011 Haince .................... C12Q 1/34
435/6.14

OTHER PUBLICATIONS

Konigshoff et al. (Clinical Chemistry, 2003, 49:2, p. 219-229).*
Hanna et al. (Mod Pathol 2001, 14(7):677-685).*
Ignatiadis et al. (Clin Cancer Res, 2008(14):2593-2600).*
Wedad M. Hanna et al., Molecular Pathology 2001; 14(7):677-685; 'Defining a Test for HER2/neu Evaluation'.
Sabine Merkelbach-Bruse et al., Surgical Pathology Dec. 2003, vol. 27, No. 12, 1565-1570; 'Current Diagnostic Method of HER2/neu Detection'.
J. Begqvist et al., Annal of Oncology Mar. 2007; 'Quantitative Real-time PCR and Micro-array-based RNA of HER2'.
ChantalTse et al., Clinical Chemistry 2005, 51:7, 1093-1101; 'evaluation of Quantitative Analytical Methods Real-time PCR for HR2'.
Stefania Gelmini et al., Clinical Chemistry 1997, 43:5, 752-758; 'Q-PCR based Assay to Measure c-erbB-2'.
Alison Millson et al., J Mol Diag, Aug. 2003, vol. 5., No. 3; 'Comparison of Two Q-PCR Methods for Detection HER2/neu Amplification'.
David G. Ginzinger et al., U.S. Pat. No. 6,180,349 B1; 'Quantitative PCR Method to Enumerate DNA Copy Number'.
Stefania Gelmini et al., Clinical Chemsitry 1997, 43:5, 752-758; 'Quantitative PCR-based homogeneous Assay with Probes to Measure c-erbB-2'.
Elisa Capizzi et al., Diagnostic Mol Pathology, Dec. 2008, vol. 17 No. 4, 220-225; 'Real Time RT-PACR Approach for the Evaluation of ERBB2'.
Ivan Bieche et al., Clinical Chemistry, 1999, 45:8, 1148-1156; 'Real-Time Reverse Transcription PCR Assay for ERBB2'.
Celine Bossard et al., Anticancer Research 25: 4679-4684 (2005); 'Real-time RT-PCR: A Complementary Method to Detect HER2'.
Carlynn Willmore et al., Apppl Immunohistochem Mol Morphol, Dec. 2005, vol. 13, No. 4; 'Correlation of HER2 Gene Amplification with IHC'.
Heidi S Erickson et al., Laboratory Investigation (2007) 87, 951-962; 'Assessment of Normalization Startegies for Q-RT-PCR'.
Sabita K. Murthy et al., Arch Pathol Lab Med, Jan. 2005, vol. 129 39-46; 'Copy Number Analysis of NER2 and TOP2A'.
Joseph A. Sparano et al., JCO, Feb. 10, 2008, vol. 26, No. 5, 721-728; 'Development of the 21-Gene Assay'.
Iker Sanchez-Navarro et al., Biotechniques May 2010, 48:389-397; 'Comparison of Gene Expression by Q-RT-PCR between FF and FFPE'.
Frederick L. Baehner et al., JCO, Oct. 1, 2010 vol. 28 No. 28, p. 4300-4306; 'Human Epidermal Growth Factor Receptor 2 Assessment'.
Massimo Barberis et al., Anatomic Pathology, 2008; 129:563-570; 'Quantitative PCR and HER2 Testing in Breast Cancer (with Paired Tissue)'.
Christophe Ginestier et al., Journal of Pathology, 2004, 202:286-298; 'Comparative Multi-methodological Measurement of ERBB2'.
J Lehmann-Che et al., British Journal of Cancer (2011) 104, 1739-1746; 'Immuno-histochemical and Molecular Analyses of HER2'.
Maureen Cronin et al., Clinical Chemistry, 2007, 53:6, 1084-1091; 'Analytical Validation of the Oncotype DX'.
David J. Dabbs et al., JCO, Nov. 10, 2011, vol. 29, No. 32, 4279-4285; 'High False-Negative Rate of HER2 of Oncotype Dx Test'.

(Continued)

*Primary Examiner* — Stephanie K Mummert
(74) *Attorney, Agent, or Firm* — Howard E. Silverman; Greenberg Traurig, LLP

(57) ABSTRACT

The present invention is related to an improved method for HER2 gene test by using quantitative real-time PCR (Polymerase Chain Reaction) technique. Our invention streamlines test process, and incorporates quality control for each major step, including sample, reagent, operation, and data report. We eliminate the need for reference genes which is hard to standardize in HER2 PCR test. We develop a cutoff reference point by using the statistical mean of tumor tissue population, and adopt a simplified scoring scheme for evaluation of HER2 status. Our invention produces consistent result across machines and labs, and has proven to be clinically successful in HER2 test.

13 Claims, 2 Drawing Sheets

(56) References Cited

OTHER PUBLICATIONS

Lise Mette Gjerdrum et al., J Mol Diagn, Feb. 2004, vol. 6, No. 1, 42-51; 'Real-time Q PCR of Microdissected FFPE Breast Carcinoma'.

Frederick L. et al., US 2010/0151463 A1; 'Method for Determining the Likelihood of Response to HER2 Inhibitors'.

Heidi S. Erikson et al., Laboratory Investigation (2007) 87, 951-962; 'Assessment of Normalization Strategies for Quantitative RT-PCR'.

Jiri Libus et al., BioTechniques 41:156-164 (Aug. 2006); 'Quantification of cDNA'.

Dirk Loeffert and Holger Engel et al., US 2012/0190026 A1; 'Method of Normalized Quantification of RNA'.

Anders Stahlberg et al., Clinical Chemistry, 2004, 50:3, 509-515; 'Properties of Reverse Transcription Reaction in mRNA Quantification'.

Helene Nortvig Abrahamsen et al., J Mol Diag, Feb. 2003; 'Towards Quantitative mRMA Analysis in PPFE using q-RT-PCR'.

* cited by examiner

FIG. 1

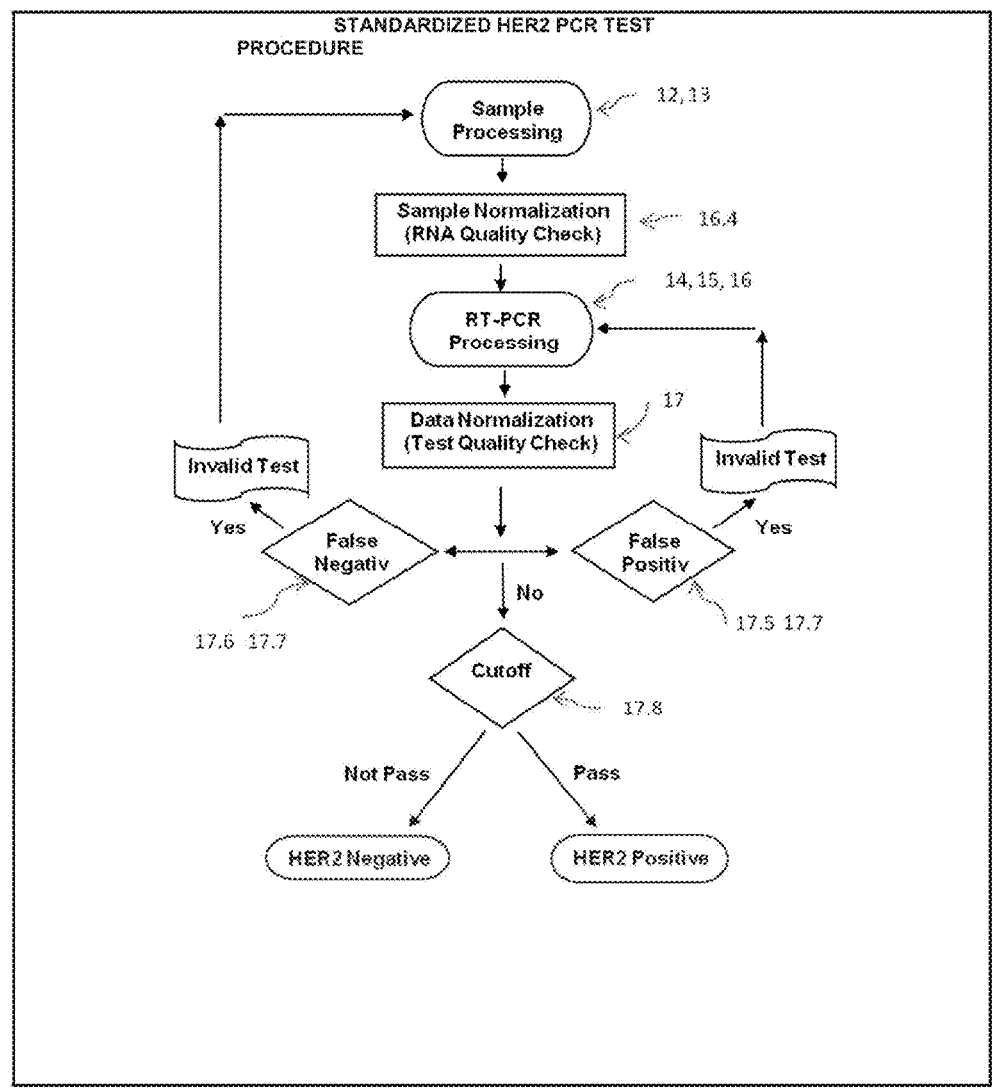

CUTOFF POINT DELTA CT. METHOD FOR HER2 PCR TESTING IN BREAST CANCER

CROSS REFERENCE TO RELATED APPLICATION

This application is a non-provisional application claiming priority from U.S. Provisional Application Ser. No. 61/598,416, filed Feb. 14, 2012.

TECHNICAL FIELDS AND BACKGROUND

Gene of human epidermal growth factor receptor 2, HER2, also known as ERBB2 or Neu, is located on chromosome 17, and shows amplification in 20% to 30% of all female breast cancers. Amplification of HER2 has been identified as a prognostic and predicative marker and also a therapeutic target for an anticancer drug, Trastuzumab (Herceptin). Many studies also have demonstrated the importance of HER2 as a marker to other types of cancers such as bladder cancer, non-small cell lung cancer, ovarian cancer, bone cancer, head and neck cancer, pancreatic cancer, prostate cancer and stomach cancer. A recent clinical trial sponsored by Roche found that the addition of Herceptin to chemotherapy increase overall survival in HER2-positive advanced stomach cancer.

Before treatment with Herceptin, it is important to determine the HER2 status accurately, because only the patients with HER2 over-expression and/or amplification benefit from the treatment. The two most widely adopted testing methods for HER2 status are immunohistochemistry (IHC) that tests HER2 protein level, and fluorescence in situ hybridization (FISH) that tests HER2 gene copies. A great advantage of these two techniques is their convenience for use on the formalin-fixed paraffin embedded tissue (FFPE), a major form of archival material. However, there are documented and published disadvantages of using IHC and FISH. The scientific disadvantages of IHC are: (1) results may be affected by tissue fixation and processing methods; (2) no standardized scoring systems exists, and disparate scoring systems have been employed, for example, some take into consideration the proportion of positive tumor cells, some only regard the intensity of staining, and other combine the two parameters into one index.

Internationally, the algorithm for HER2 testing is to perform IHC to assess HER2 over-expression, in which patients with equivocal HER2 expression (2+) are further tested to assess HER2 amplification using FISH method, or patients are initially assessed for HER2 status by FISH method. FISH methods approved by US Food and Drug Administration (US-FDA) for predicting the effect of Herceptin therapy depend on the ratio between HER2 gene and chromosome 17, which distinguish HER2 gene amplification from chromosome 17 aneusomy.

The scientific disadvantages of FISH are: (1) possible HER2 over-expression by single gene not detectable, (2) difficulties associated with identification of invasive tissue (hard to identify the correct cells to count due to the lack of conventional morphologic features in the tissue), (3) difficult interpretation of borderline amplification, (4) temporary nature of staining due to the fluorescence signal fades over time. From the cost and benefit point of view, FISH is more expensive than IHC, because of the need for a fluorescence microscope, high cost of reagents, and lengthy processing time. CISH (Chromogenic In situ Hybridization) and SISH (Silver In situ Hybridization) are two emerging techniques which also measure gene copies in tumor cells.

Real-time or quantitative PCR (Polymerase Chain Reaction) has emerged as a superior alternative to the existing HER2 testing methods because of its high accuracy, wide dynamic range, and easy operation. Real-time PCR, a technology that is originally designed to measure mRNA expression level in cells, has been applied in detecting infectious diseases such as AIDS and SARS, and begins to make its way into the molecular diagnostics arena. There are some PCR-based test kits approved by US-FDA and seen to be used in 'home brew' or CLIA (Clinical Laboratory Improvement Amendments) certified laboratories. One good example is Oncotype Dx test which was approved by FDA under CLIA to perform PCR test for a number of breast cancer genes including HER2 at Genomic Health reference lab. There is no known FDA-approved HER2 PCR test kit for general clinical use at this time.

RELEVANT PRIOR ART AND U.S. PATENTS

There have been many publications about the high degree of concordance between PCR and FISH in HER2 test results since 1994. However, there has been no FDA approved PCR HER2 test kit for test labs use at the present time for the following reasons:

Different scoring systems and cutoffs have been used in assessing HER2 studies. Unlike FISH and IHC which have worldwide clinical recognition and adoption to the established cutoff value for HER2 positive, most of the publications in HER2 PCR test used varied biomarkers either DNA or mRNA, varied reference genes and varied mRNA normalization methods that produce HER2 test data without a cutoff value or the cutoff varied widely based on the chosen methods. This variability makes clinical adoption of HER2 PCR test difficult if not impossible. The issue of the technical variability in HER2 PCR test was pointed out by the editorial of the Journal of American Society of Clinical Oncology in August of 2010.

Lack of standard in quality control from sample preparation to PCR operation that handicaps the reproducibility of the test results. There was an initiative from MIQE (Minimum Information for Publication of Quantitative Real-Time PCR Experiments) Guideline in 2009 from Clinical Chemistry; however, MIQE's emphasis is more on publication consistency and transparency rather than PCR clinical application viability.

We reviewed the state of art here with a focus on the best practice or standardization of PCR technology to HER2 gene expression testing in a clinical setting, and not the HER2 gene or the PCR quantification technology such as primer and probe design, nor the treatment of HER2 over-expression. Most if not all the relevant references to this invention can be found in the field of chemistry, pathology, molecular diagnostics and oncology. Key word search on HER2 PCR hits many matches in the USPTO database. However, the three that are most relevant are referenced herein.

The application of PCR technology to HER2 testing started in 1990's with DNA as a biomarker. Various reference genes were used extensively for data normalization (See for example: Wedad M. Hanna et al., Molecular Pathology 2001; 14(7):677-685; 'Defining a Test for HER2/neu Evaluation'; Sabine Merkelbach-Bruse et al., Surgical Pathology December 2003, Vol 27, No. 12, 1565-1570; 'Current Diagnostic Method of HER2/neu Detection'; J. Begqvist et al., Annal of Oncology March 2007; 'Quantitative Real-time PCR and Micro-array-based RNA of HER2'; ChantalTse et al., Clinical Chemistry 2005, 51:7, 1093-1101; 'evaluation of Quantitative Analytical Methods Real-time PCR for HR2'; Stefania Gelmini et al., Clinical Chemistry 1997, 43:5, 752-758; 'Q-PCR based Assay to Measure c-erbB-2'; Alison Millson et al., J Mol Diag, August 2003, Vol 5, No. 3; 'Comparison of Two Q-PCR Methods for Detection HER2/neu Amplification'; David G. Ginzinger et al., US6,180,349 B1; 'Quantitative PCR Method to Enumerate DNA Copy Number'; and Stefania Gelmini et al., Clinical Chemsitry 1997, 43:5, 752-758; 'Quantitative PCR-based homogeneous Assay with Probes to Measure c-erbB-2'.). Over time, HER2 biomarker was extended to mRNA with the similar methods (See, for example: Elisa Capizzi et al., Diagnostic Mol Pathology, December 2008, Vol 17 No. 4, 220-225; 'Real Time RT-PACR Approach for the Evaluation of ERBB2'; Ivan Bieche et al., Clinical Chemistry, 1999, 45:8, 1148-1156; 'Real-Time Reverse Transcription PCR Assay for ERBB2'; Celine Bossard et al., Anticancer Research 25: 4679-4684 (2005); 'Real-time RT-PCR: A Complementary Method to Detect HER2'; Carlynn Willmore et al., Apppl Immunohistochem Mol Morphol, December 2005, Vol 13, No. 4; 'Correlation of HER2 Gene Amplification with IHC'; Heidi S Erickson et al., Laboratory Investigation (2007) 87, 951-962; 'Assessment of Normalization Startegies for Q-RT-PCR'; Sabita K. Murthy et al., Arch Pathol Lab Med, January 2005, Vol 129 39-46; 'Copy Number Analysis of NER2 and TOP2A'; Joseph A. Sparano et al., JCO, Feb. 10, 2008, Vol 26, No. 5, 721-728; 'Development of the 21-Gene Assay'; Iker Sanchez-Navarro et al., Biotechniques May 2010, 48:389-397; 'Comparison of Gene Expression by Q-RT-PCR between FF and FFPE'; Frederick L. Baehner et al., JCO, Oct. 1, 2010 Vol 28 No. 28, P 4300-4306; 'Human Epidermal Growth Factor Receptor 2 Assessment'; Massimo Barberis et al., Anatomic Pathology, 2008; 129:563-570; 'Quantitative PCR and HER2 Testing in Breast Cancer (with Paired Tissue)'; Christophe Ginestier et al., Journal of Pathology, 2004, 202:286-298; 'Comparative Multi-methodological Measurement of ERBB2'; J Lehmann-Che et al., British Journal of Cancer (2011) 104, 1739-1746; 'Immuno-histochemical and Molecular Analyses of HER2'; Maureen Cronin et al., Clinical Chemistry, 2007, 53:6, 1084-1091; 'Analytical Validation of the Oncotype DX'; David J. Dabbs et al., JCO, Nov. 10, 2011, Vol 29, No. 32, 4279-4285; 'High False-Negative Rate of HER2 of Oncotype Dx Test'; Lise Mette Gjerdrum et al., J Mol Diagn, February 2004, Vol 6, No. 1, 42-51; 'Real-time Q PCR of Microdissected FFPE Breast Carcinoma'; Frederick L. et al., US 2010/0151463 A1; 'Method for Determining the Likelihood of Response to HER2 Inhibitors'; and Heidi S. Erikson et al., Laboratory Investigation (2007) 87, 951-962; 'Assessment of Normalization Strategies for Quantitative RT-PCR'.). Most of those studies had no specific HER2 overexpression cutoff point established. However, a few studies suggested use statistical means of HER2 expression of normal breast cancer tissue, plus between 2 to 5 standard deviations as a base for HER2 positive cutoff point. There have been no reference on how to apply the suggested cutoff point method the same manner to different processed forms of breast tumor tissue, i.e., frozen vs. paraffin.

Total RNA have been mentioned as an alternative to reference gene in data normalization, but no reference has been found to apply the total RNA method to HER2 PCR testing application (See for example: Jiri Libus et al., BioTechniques 41:156-164 (August 2006); 'Quantification of cDNA'; Dirk Loeffert and Holger Engel et al., US 2012/0190026 A1; 'Method of Normalized Quantification of RNA'; Anders Stahlberg et al., Clinical Chemistry, 2004, 50:3, 509-515; 'Properties of Reverse Transcription Reaction in mRNA Quantification'; and Helene Nortvig Abrahamsen et al., J Mol Diag, February 2003; 'Towards Quantitative mRMA Analysis in PPFE using q-RT-PCR'.).

This invention is to present a streamlined HER2 PCR test process with built-in quality check at each major step, and with a simplified test scoring system for HER2 status. We adopt total RNA as a one for all tools instead of reference genes in HER2 expression data normalization to minimize sample variability. We intend to establish a robust, easy to use, and easy to standardize HER2 real-time PCR testing procedure for either the frozen specimens or the paraffin specimens. The combination and the sequence of the methods that we have put together was not found in our prior art search. We have proved the clinical utility of our invention with clinical data, and adoption of our invention will lead to development of a new clinical test to offset the weakness of current HER2 test methods.

SUMMARY

We have invented a procedure that codifies the observed behavior of tumor tissue population statistics in the external calibration curve (or standard curve) or reaction PCR well for absolute PCR quantification analysis. Our method enables to normalize the variability across intra/inter lab testing, among different makes of PCR machines and various experimental conditions. Most importantly, our method can pre-determine a cutoff point with 95% confidence based on statistics and validated by HER2 test gold standard FISH method. Our normalization and cutoff point methodology is simple but consistent for gene expression analysis in cancer diagnostics, and may serve as a standard for adoption.

BRIEF DESCRIPTION OF THE DRAWINGS

FIG. 1 is an example plate setup format.

FIG. 2 is a flowchart of an example HER2 PCR testing procedure

DETAILED DESCRIPTION

Method

Sample Collection—Immediately after biopsy or surgery, the tumor specimen can be preserved in formalin-fixed paraffin embedded (FFPE), freshly frozen in liquid nitrogen or in optimal-cutting temperature compound (OCT).

RNA Extraction—The total RNA is extracted from 25 mg of frozen sample or from ten 10-μm sections by using a commercial RNA Isolation Kit. The total RNA concentration was determined by a spectrophotometer or fluorometer.

Reagent Content—Reagents are stored at −20° C. in two groups. HER2 sDNA is a synthetic single-stranded oligo nucleotide, and has a molecular weight of 22570.6. Control RNA is prepared from breast cancer cell lines.

Pack A:

RT Mix (650 μl)
PCR Mix (4400 μl)
RT Enzyme (200 U/μl, 12 μl)
PCR Enzyme (5 U/μ, 25 μl)
RNase/DNase-free water (500 μl)
tRNA solution (0.1 mg/ml, 50 μl)
Control RNA (80 μl, at 25 ng/μl)

-continued

Pack B:

Her-2 sDNA (0.2 pg/μl, 50 μl)
Her-2 sDNA (0.02 pg/μl, 50 μl)
Her-2 sDNA (0.002 pg/μl, 50 μl)
Her-2 sDNA (0.0002 pg/μl, 50 μl)
Her-2 sDNA (0.00002 pg/μl, 50 μl)

Figure 1:
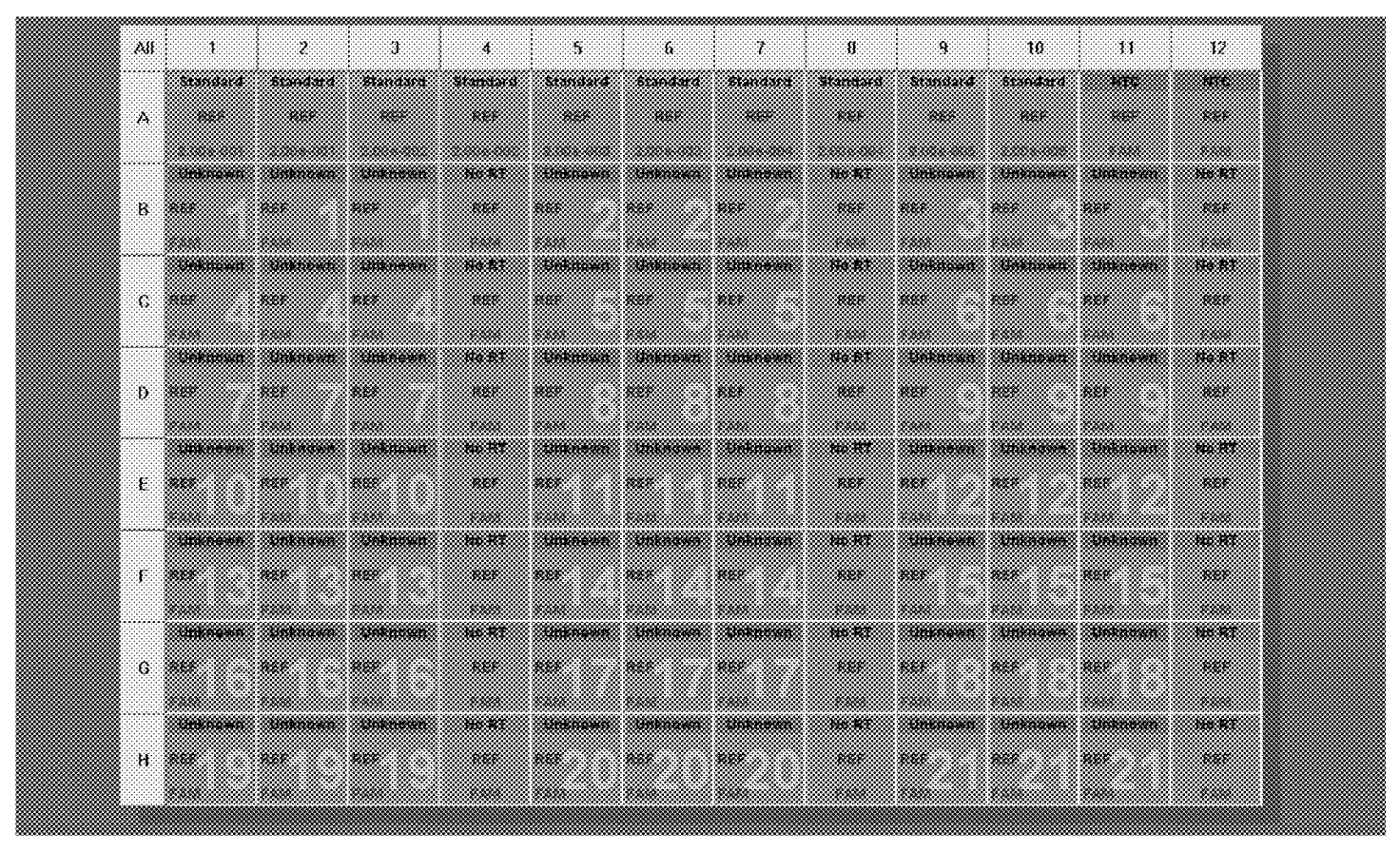

Assay and Plate Design—A HER2 test contains the reactions: i) sDNA solutions and one NTC in duplicate for generation of Standard Curve; ii) Unknown sample RNA in triplicate, plus one No RT well for each sample; iii) Control RNA in triplicate plus one No RT well. Refer to the User Manual of real-time PCR machine for the procedures of assigning plate wells for the above reactions. Choose 'FAM' for Collect fluorescence data and 'ROX' as Reference dye. See FIG. 1 for an example of plate setup.

Running RT and PCR—Real-time PCR assay consists of two consecutive steps, i.e., reverse transcription (RT) and polymerase chain reaction (PCR). In RT process, mRNA is converted to a single stranded cDNA which is then amplified with a specific pair of primers in PCR process. The quantity of amplified DNA fragments is monitored with a fluorescence-labeled oligo probe in each PCR cycle. The $C_t$ value is recorded for each amplification curve, and is used for calculation of gene expression level in sample. Following are detailed steps.

1. Take out RT Mix, RT enzyme, tRNA, and water from Pack A, and thaw them on ice; meanwhile, take out sDNA solutions from Pack B and put them on a separate ice bath. Invert each vial several times after thawing reagent.
2. Determine the number of reactions for your assay and calculate the quantity of RT Mix and RT Enzyme. For each reaction, including Standard, Unknown, NTC and No RT, you need 5.9 μl RT Mix and 0.1 μl RT Enzyme, but in No RT control, add 0.1 μl water to replace RT Enzyme. Mix solution by pipeting up and down for several times. Do not vortex.
3. Load 6 μl of the above solution to each well uniformly. It is not necessary to change tip after each loading.
4. Determine RNA concentration for each sample and adjust to 25 ng/μl. Add 4 μl of RNA sample to each Unknown or No RT well, the total RNA in each reaction will be 100 ng; meanwhile, add 4 μl of Control RNA to each 'Control RNA' well.
5. Add 4 μl of sDNA solution to each corresponding Standard well. In NTC well, add 4 μl of tRNA to replace sDNA. The total volume of each RT reaction is 10 μl.
6. Seal PCR plate tightly with membrane across plate edges and around each well. Put the plate into real-time PCR machine and perform RT reaction using a thermal profile: 50° C. for 30 min, and 72° C. for 5 min, then cool down to 20° C. or room temperature.
7. When running RT, take out PCR Mix and PCR Enzyme from Pack A. Thaw the reagents on ice, and re-suspend the reagents by inverting vials several times.
8. Calculate the quantity of PCR Mix and PCR Enzyme needed for your assay. For each PCR reaction, you need 39.8 μl of PCR Mix and 0.2 μl of PCR Enzyme. Add appropriate amount of PCR enzyme to PCR Mix, and pipet solution up and down several times. Do not vertex solution.
9. Load 40 μl of above solution to each well. Seal PCR plate again with membrane and ensure that the edges and wells are tightly sealed. The total volume of solution in each well will be 50 μl.
10. Put the plate back to a real-time PCR machine and set up thermal profile to: 95° C. for 1 min/40 cycles of 95° C. for 12 s/55° C. for 1 min/72° C. for 30 s.
11. Collect data after running, and trash the plate in a different location to avoid potential contamination to the future assays.

Data Analysis and Test Requirements—Our method offers a tool for accurate measurement of HER2 expression level in breast cancer cells, as well as a tool for identification of cancer patients who might benefit from Herceptin treatment. Tests of breast tumor samples lead to establishment of a cutoff reference point for HER2 positive tumors. Following is detailed discussion on obtaining high quality test results.

1. Threshold setup. Threshold is defined as a fluorescence intensity level, above which the fluorescence signal is considered to be significantly higher than the background. Software provided with real-time machine setup a threshold following each PCR run for calculation of sample $C_t$. However, the threshold will vary in different assays. Our tests indicate that sDNA at 0.002 ng/μl has an average $C_t$ of 21.65 (Table 1); accordingly, setup of a threshold to yield a $C_t$ value of 21.65 for 0.002 sDNA will produce consistent results across assays.
2. Validation of standard curve. Standard Curve is a plot of the initial template quantity in the standard wells (X-axis) versus the $C_t$ (threshold cycle). Usually, a least mean square curve fitting algorithm is adopted to generate a standard curve. $R^2$ is a key parameter used to evaluate the quality of a standard curve. The highest value of $R^2$ is 1. Standard curve that has a $R^2$ value higher than 0.95 is considered valid.
3. Amplification Efficiency. Amplification Efficiency measures the percentage of the template molecules which are doubled every cycle, and is a comprehensive parameter that reflects the overall quality of assay reagents and conditions. In a real-time PCR, amplification efficiency is estimated from standard curve using the equation: Efficiency=$10^{(-1/slope)}-1$. A valid assay should have an Amplification Efficiency above 95%.
4. Replicate Variation. Replicates are wells which contain the same RNA sample, and, theoretically, should have the same $C_t$ value. Therefore, variation among the replicates would represent the errors of assay operations. A valid test should have a replicate variation of less than 0.5 $C_t$ units.
5. False Positive. If a sample contains normal level of HER2 mRNA but displays a significantly low $C_t$, this phenomenon is termed as 'False Positive'. A major cause of false positive sample is DNA contamination, which may come from many different sources, such as reagents and amplified products from neighboring wells or previous assay plates. A "No Template Control' (NTC) is included in the test for each sample, and should have no amplification signal or no $C_t$ under normal conditions.
6. False Negative. If a sample contains an over-expression level of HER2 mRNA but displays a normal or even higher $C_t$, this phenomenon is termed as 'False Negative'. The sample quality is a major cause of false negative results. For example, the presence of PCR inhibitors or RNA degradation can lead to high shift of $C_t$ value. Our tests indicate that effects of both PCR inhibitors and RNA degradation are highly sensitive to sample dilution. If a sample at two different concentrations shows consistent result, then, it is considered having acceptable quality.

7. Control RNA. Test also incorporates control RNAs which are isolated from breast cancer cell lines. These RNAs are used as true controls for HER2 positive and HER2 negative. Inclusion of these RNAs also monitors reagent quality and assay operation. Under standard test conditions, control RNAs show constant delta $C_t$ value ($\Delta C_t$) against cutoff reference point.

8. Cutoff Reference Point. Prior to routine HER2 PCR testing, a HER2 cutoff reference point(s) (CRP) must be established in order to compute the $c\Delta C_t$ which is equal to CRP—$C_t$ (Unknown Sample); if $c\Delta C_t>1$, the test result is HER2 positive; else, negative. CRP is derived from the statistical mean of a breast tumor tissue population, and is monitored by a synthetic DNA (sDNA) in each test.

Validation with FISH Test—HER2 gene amplification was determined by the FDA-approved Pathway Her2 DNA Probe Kit (Vysis/Abbott, USA). According to the manufacturer's instruction, HER2 gene was considered non-amplified if an average Her2 (red) to CEP17 (green) ratio was <2.0, and low amplification between 2.0 and 4.0, and highly amplified if the ratio was >4.0. For comparison purpose, the samples with a ratio of ≥2.0 were classified as HER2 positive; otherwise, as HER2 negative. FISH tests were conducted either at NCKU Pathology Lab or by an outsourced reference lab. FISH test were done selectively (mostly for IHC 2+ samples), not for all the samples.

EXAMPLES

Testing Procedure Flow Chart—FIG. 2 is included to demonstrate the essence of the quality assurance and result validation before and after the PCR run with the invented cutoff point method.

Test Data and Result Analysis—Table 1 shows establishment of HER2 standard curve baseline and calculation of $c\Delta C_t$, for the determination of HER2 expression status in breast tissue samples. As detailed in 'Claim 10', if $c\Delta C_t$ is greater than 1, then HER2 test is positive; otherwise, the HER2 test will be negative. The cutoff reference point (CRP) for the tissues preserved in optimal-cutting temperature compound (OCT) is 21.65, for the tissues in formalin-fixed paraffin embedded (FFPE) is 25.13. Tissue samples from sources, such as OCT vs. FFPR, can be tested in the same PCR run.

Distribution of HER2 mRNA Expression in Breast Tissues—Table 2 shows that HER2 mRNA gene expression in both tumor and normal tissues exhibits a normal distribution, regardless the tissue processing methods. Analysis also shows that HER2 expression in the tumor in normal tissues belongs to different populations. Showing a normal distribution of HER2 mRNA expression offers a statistical basis for establishment of cutoff reference point (CRP) for HER2 PCR testing.

Establishment of Cutoff Reference Point (CRP) by using The Statistical Mean of Breast Tumor HER2 mRNA expression level. Table 3 shows adoption of a $C_t$ value as cutoff reference point that is around the statistical mean of HER2 mRNA expression level in the tumor samples and is equivalent the statistical mean of normal tissue minus 3.5 standard deviation. Given that the statistical mean varies by sample sources, such as OCT vs. FFPE, different CRP is used for different tissue sources accordingly. Table 3 also shows that CRP may be monitored by a defined quantity of sDNA (a synthetic single-stranded DNA) in each test for easy calculation of $c\Delta Ct$ in a real-time manner, which is further described in 'Claim 10'.

Test Result Validation, PCR vs. FISH—Table 4 shows the detail test results of the invented method and FISH method on different types and sources of breast tumor samples. Table 5 is included to summarize the agreement score between the invented method and the existing FISH method. Given that the sample acquisition in this study is random and non-consecutive slicing between the PCR test and the FISH test for the same patient, the agreement score of 90% reported here is conservative.

With Reference to FIG. 1, it will be noted that 'Standard' is the well containing different amount of Her-2 sDNA for generation of Standard Curve; 'Unknown' is the well that contains sample RNA, and each sample is run in triplicate; 'NTC' is a control which contains all the reaction components except sDNA; 'No RT' is a control which contains RNA and all other reaction components, but no RT enzyme; 'Control RNA' is included as control for the quality of both RT and PCR reactions.

TABLE 1

HER2 PCR Test Result Analysis
Sample Test Result

| sDNA Dilution | | Baseline Avaerage Ct. | Test Result Ct. | Variance with Baseline | cΔCt | PCR HER2 Test Result |
|---|---|---|---|---|---|---|
| 0.2 | | 15.21 | 14.73 | −3.16% | | |
| 0.02 | | 18.40 | 18.45 | 0.25% | | |
| 0.002 * | | 21.65 | 21.94 | 1.34% | | |
| 0.0002 ** | | 25.13 | 24.60 | −2.10% | | |
| 0.00002 | | 28.38 | 28.05 | −1.17% | | |
| RT Control - 1 | | 24.84 | 24.82 | −0.08% | | |
| Delta Ct. * | | −3.19 | −2.88 | −9.69% | | |
| Sample 1 IHC 3+ | Tumor | OCT | 20.58 | | 136 | Positive |
| | | FFPE | 23.49 | | 1.11 | Positive |
| | Normal | OCT | 25.92 | | | |
| | | FFPE | 29.03 | | | |
| Sample 2 IHC 1+ FISH− | Tumor | OCT | 24.67 | | −2.73 | Negative |
| | | FFPE | 26.08 | | −1.48 | Negative |
| | Normal | OCT | 25.84 | | | |
| | | FFPE | 28.68 | | | |
| Sample 3 IHC 2+ FISH− | Tumor | OCT | 23.97 | | −2.03 | Negative |
| | | FFPE | 26.51 | | −1.91 | Negative |
| | Normal | OCT | 27.97 | | | |
| | | FFPE | 28.27 | | | |

HER2 Tumor Tissue Positive Baseline :

OCT Ct. = 21.65

FFPE Ct. = 25.13

TABLE 2

HER2 mRNA Expression in Breast Cancer

| | | Tumor vs. Normal Tissues | | | Combined Tumor and Normal Tissues Oct. 6, 2012 | | | | | | |
|---|---|---|---|---|---|---|---|---|---|---|---|
| | | FFPE | | OCT | | | FFPE | | | OCT | |
| | | Frequency | | Frequency | | | Cum | | | Cum | |
| | Ct | Tumor | Normal | Tumor | Normal | Ct. Range | Feq | Feq | CF % | Feq | Feq | CF % |
| | 16 | 0 | 0 | 0 | 0 | 0-15 | 0 | 0 | 0.00% | 0 | 0 | 0.00% |
| | 18 | 0 | 0 | 4 | 0 | 16-18 | 0 | 0 | 0.00% | 4 | 4 | 5.00% |
| | 20 | 6 | 0 | 6 | 0 | 19-20 | 6 | 6 | 7.50% | 6 | 10 | 12.50% |
| | 22 | 6 | 0 | 4 | 1 | 21-22 | 6 | 12 | 15.00% | 5 | 15 | 18.75% |
| | 24 | 11 | 1 | 17 | 1 | 23-24 | 11 | 23 | 28.75% | 18 | 33 | 41.25% |
| | 26 | 5 | 6 | 4 | 7 | 25-26 | 6 | 29 | 36.25% | 11 | 44 | 55.00% |
| | 28 | 9 | 22 | 3 | 15 | 27-28 | 15 | 44 | 55.00% | 18 | 62 | 77.50% |
| | 30 | 3 | 8 | 2 | 10 | 29-30 | 25 | 69 | 86.25% | 12 | 74 | 92.50% |
| | 32 | 0 | 3 | 0 | 6 | 31-32 | 8 | 77 | 96.25% | 6 | 80 | 100.00% |
| | 34 | 0 | 0 | 0 | 0 | 33-34 | 3 | 80 | 100.00% | 0 | | |
| | Sum | 40 | 40 | 40 | 40 | Sum | 80 | | | 80 | | |
| Noemality | R2 | 0.991 | 0.984 | 0.986 | 0.984 | R2 | | 0.971 | | | 98.90% | |
| Test | 95% CICV | 0.971 | 0.971 | 0.971 | 0.971 | 95% CICV | | 0.984 | | | 98.40% | |

Note:
Breast cancer tumor or normal tissue HER2 expression is normal distribution
Combined tumor and normal tissue HER2 expression is bimodal with two peaks
Cutoff Control Value 0.002 Ct 21.65 0.0002 Ct. 25.13

TABLE 3

Breast Cancer TumorHER2 mRNA Statistical Mean and Cutoff Point
Cutoff Analysis (40 Pairs)

| | FFPE | | | OCT | | |
|---|---|---|---|---|---|---|
| | Tumor | Normal | Cutoff | Tumor | Normal | Cutoff |
| Mean (N = 40 Pairs) | 23.86 | 29.17 | | 22.40 | 27.64 | |
| Std Dev (N = 40 Pairs) | 2.51 | 1.11 | | 2.34 | 1.60 | |
| Mean (N = 54 OCT; 63 FFPE) | 24.21 | | | 21.86 | | |
| Std Dev (N = 54 OCT; 63 FFPE) | 2.54 | | | 2.45 | | |
| RefsDNA (Calibrator) | 25.13 | | | 21.65 | | |
| Comp T/N Ratio | | -4.79 | | | -3.28 | |
| T/N Ratio = 3 Std Dev | | | 25.84 | | | 22.84 |
| T/N Ratio = 4 Std Dev | | | 24.73 | | | 21.24 |
| T/N Ratio = 5 Std Dev | | | 23.62 | | | 19.64 |

T/N Ratio = (Tumor Tissue Mean − Normal Tissue Mean)/Normal Tissue Std Dev
Cutoff Ref = Normal Tissue Mean − (T/N Ratio) * Normal Tissue Std Dev or = Tumor Tissue Mean

TABLE 4

HER2 PCR Test Results Validation with FISH
Phase 1 Tissue Pathology Report

| | | | | Test Results | | | | |
|---|---|---|---|---|---|---|---|---|
| Phase | Case | | | PCR | PCR | Sample | Tumor Sample Content | |
| No. | No. | IHC | FISH | OCT | FFPE | Source | OCT | FFPE |
| 1 | 1 | 2+ | FP+ | 5.16 | 4.86 | Surgery | ? | IDC 90% |
| 1 | 2 | 2+ | FP+ | 4.12 | -0.26 | Surgery | DCIC 85% | IDC 50% |
| 1 | 3 | 2+ | FP+ | 3.77 | 3 | Surgery | IDC 80% | IDC 80% |
| 1 | 4 | 2+ | FP+ | 3.71 | 0.57 | Surgery | IDC 90% | IDC 20% |
| 1 | 5 | 3+ | FP+ | 2.92 | 4.97 | Surgery | IDC 50% DCIC 30% | IDC 60% DCIS 20% |
| 1 | 6 | 2+ | FN− | 2.45 | 3.35 | Surgery | IDC 70% DCIC 10% | IDC 80% DCIC 10% |
| 1 | 7 | 2+ | FP+ | 1.7 | 3.19 | Surgery | IDC 30% necrosis 10% | IDC 70% DCIS 20% |
| 1 | 8 | 2+ | FN− | 1.48 | 1.98 | Surgery | IDC 100% | IDC 80% |
| 1 | 9 | 2+ | FN− | 0.83 | -0.7 | Surgical | IDC 65% | IDC 40% DCIS 50% |
| 1 | 10 | 0 | FN− | 0.79 | -0.34 | Surgery | DCIC 80% | DCIS 30% |
| 1 | 11 | 2+ | FN− | 0.03 | 6.14 | Surgery | ILC 40% | IDC 50% |
| 1 | 12 | | FP+ | -0.04 | N/A | Surgery | ? | IDC 100% |
| 1 | 13 | 1+ | FN− | -0.72 | 0.61 | Surgery | IDC 100% | IDC 100% |
| 1 | 14 | 2+ | FN− | -7.45 | -2.57 | Surgery | IDC 20% | IDC 25% |

TABLE 4-continued

HER2 PCR Test Results Validation with FISH
Phase 1 Tissue Pathology Report

| Phase No. | Case No. | Test Results | | PCR OCT | PCR FFPE | Sample Source | Tumor Sample Content | |
|---|---|---|---|---|---|---|---|---|
| | | IHC | FISH | | | | OCT | FFPE |
| 1 | 15 | 3+ | FP+ | | 4.7 | Biopsy | | IDC 30%, DCIC 20% |
| 1 | 16 | 3+ | FP+ | | 4.62 | Biopsy | | IDC 90% |
| 1 | 17 | 3+ | FP+ | | 4.41 | Biopsy | | IDC 60%, DCIS 20% |
| 1 | 18 | 3+ | FP+ | | 4.12 | Biopsy | | IDC 100% |
| 1 | 19 | 3+ | FP+ | | 3.86 | Biopsy | | IDC 70% |
| 1 | 20 | 2+ | FP+ | | 2.69 | Biopsy | | IDC 50%, DCIS 50% |
| 1 | 21 | 3+ | FP+ | | 1.75 | Biopsy | | IDC 100% |
| 1 | 22 | 3+ | FP+ | | 1.19 | Biopsy | | IDC 10%, DCIS 70% |
| 1 | 23 | 3+ | FP+ | | 0.98 | Biopsy | | IDC 70%, DCIS 10% |
| 1 | 24 | 2+ | FN− | | 0.66 | Biopsy | | IDC 80% |
| 1 | 25 | 3+ | FN− | | 0.15 | Biopsy | | IDC 90% |
| 1 | 26 | 2+ | FN− | | 0.04 | Biopsy | | IDC 30%, DCIS 60% |
| 1 | 27 | 3+ | FN− | | −0.87 | Biopsy | | IDC 80%, DCIS 10% |
| 1 | 28 | 3+ | FP+ | | −1.39 | Biopsy | | IDC 70% |
| 1 | 29 | 1+ | FN− | | −1.74 | Biopsy | | IDC 80% |
| 1 | 30 | 1+ | FN− | | −1.37 | Biopsy | | 80% IDC |
| 1 | 31 | 3+ | FN− | | −2.78 | Biopsy | | IDC 60%, DCIS 10% |
| 1 | 32 | 3+ | FN− | | −2.86 | Biopsy | | IDC 100% |
| 1 | 33 | 2+ | FN− | | −4.81 | Biopsy | | IDC 40% |
| 1 | 34 | 3+ | FN− | | −10.29 | Biopsy | | DCIS 10% Samples Are Excluded |

DCIS: Ductal Carcinoma In Situ
IDC: Invasive Ductal Carcinoma
ILC: Invasive Lubular Carcinoma

TABLE 5

HER2 PCR Test Results and FISH Test Result Concordance Study
HER2 PCR vs FISH Test RESULTS (EXLCUDE NON-IDC DATA)

| | | | Test Results | | | Clinical Outcome | | | | Disagreement | Agreement Score | | |
|---|---|---|---|---|---|---|---|---|---|---|---|---|---|
| | | | Positive | Negative | Sum | Sensitivity | Specificity | PPV | NPV | Count | PPA | PNA | OPA |
| | | FISH Test | | | | | | | | | | | |
| PCR Test | FFPE from Same Biopsy | Positive Negative | 9 1 | 1 8 | 10 9 | 90% | 90% | 11% | 10% | 2 | 90% | 89% | 89% |
| | FISH Test Samples | Sum | 10 | 9 | 19 | | | | | | | | |
| | FFPE from All Sources | Positive Negative | 15 5 | 6 28 | 21 33 | 75% | 82% | 18% | 25% | 11 | 75% | 82% | 80% |
| | | | 20 | 34 | 54 | | | | | | | | |
| | OCT from All Sources | Positive Negative | 9 2 | 2 21 | 11 23 | 82% | 91% | 9% | 18% | 4 | 82% | 91% | 88% |
| | | Sum | 11 | 23 | 34 | | | | | | | | |

PPV: Positive Predictive Value (False Positive);
NPV: Negative Predictive Value (False Negative)
PPA: Positive Percentage AGreement;
PNA: Negative Percentage Agreement;
OPA: Overall Percentage Agreement

The invention claimed is:

1. A streamlined and standardized method for determining the HER2 status of a tumor sample by measuring HER2 mRNA expression level using quantitative real-time PCR technique a simplified scoring system without use of reference genes, and comprising the steps of:
   (a) preparing a specimen sample with invasive cancer content for HER2 test;
   (b) extracting total RNA from the specimen sample and measuring its concentration;
   (c) running reverse transcription and PCR with a constant amount of total RNA for cDNA input along with synthetic oligos (sDNA) as a reference material having at least one embedded cutoff reference point (CRP) and without using a reference gene and wherein the CRP is defined in terms of a specify copy number of HER2 mRNA; and
   (d) analyzing the mRNA output of the PCR analysis by applying the dynamic and normalized cutoff reference point reading to score the result as HER2 positive or HER2 negative.

2. The method of claim 1, wherein the specimen sample can be flexible, depending on its availability and wherein the specimen sample can be freshly-frozen tissue (FF), freshly frozen optimal-cutting-temperature-compound tissue (FF OCT), or formalin-fixed paraffin-embedded tissue (FFPE) and wherein the specimen sample is cut at 10 to 25 mg for FF tissue and ten 10-μm for FF OCT or FFPE tissue.

3. The method of claim 1, wherein different sources of specimen samples source can be tested on the same PCR plate.

4. The method of claim 1, wherein sample RNA input to each reaction is constant in volume (i.e., 4 μl) diluted concentration of 25 ng/μl and wherein the testing of a sample offers a simple but effective tactic for sample quality control.

5. The method of claim 1, wherein sDNA is prepared at various concentrations to cover the full range of HER2 mRNA expression levels for multiple types of tumor tissues.

6. The method of claim 1, wherein the cutoff reference point is the statistical mean and standard deviations of the normal specimen tissue mRNA expression.

7. The method of claim 1, wherein a dual RNA control system is implemented for scoring the result as HER2 positive or HER2 negative, to provide quality check for potential false reading arising from technical defects in reagents and testing procedures and wherein control RNAs are prepared from breast cancer cell lines.

8. The method of claim 1, wherein the HER2 PCR test results of step (d) will be scored in terms of Ct, threshold cycle at which the PCR instrument first detects fluorescence above background noise.

9. The method of claim 1, wherein the Ct of test result of step (d) is adjusted for experimental variance and for cutoff reference check with the following equations:

$$c\Delta Ct = Ct(\text{CRP}) - Ct(\text{Unknown Sample});$$

if $c\Delta Ct > 1$, the HER2 test result is HER2 positive;

else, the HER2 test result is HER2 negative.

10. The method of claim 1, wherein the HER2 status by PCR test of step (d) is validated with FISH companion test and wherein the valid test results are ranged between 85% and 95% in agreement, which will depend on sample forms and tumor biological heterogeneity tested and wherein, if adjacent tumor slices from the same tumor block are used for RT-PCR and for FISH, the agreement between two test results will be the highest.

11. The method of claim 1, wherein the cancer tumor is a breast cancer.

12. The method of claim 1, wherein the cancer tumor can be any cancers where HER2 expression needs to be tested for treatment decision making and wherein the HER2 mRNA expression is a normal distribution statistically; whereby the CRP concept is applicable to HER2 test in other cancers.

13. The method of claim 1, wherein HER2 can be tested by using the circulating tumor cell mRNA obtained from blood sample and wherein the Cutoff Reference Point for HER2 mRNA expression can be set at a level corresponding to 15 ng/ml of HER2 protein as determined by an Enzyme-linked Immunosorbent Assay kit.

* * * * *